United States Patent
Dubs

(10) Patent No.: US 11,313,847 B2
(45) Date of Patent: Apr. 26, 2022

(54) METHOD AND APPARATUS FOR IN SITU CEMENT CURING

(71) Applicant: Halliburton Energy Services, Inc., Houston, TX (US)

(72) Inventor: Liam Dubs, Fort Worth, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 169 days.

(21) Appl. No.: 16/561,813

(22) Filed: Sep. 5, 2019

(65) Prior Publication Data

US 2021/0072217 A1    Mar. 11, 2021

(51) Int. Cl.
*G01N 33/24*    (2006.01)
*E21B 49/02*    (2006.01)
*E21B 43/116*   (2006.01)

(52) U.S. Cl.
CPC ............. *G01N 33/24* (2013.01); *E21B 49/02* (2013.01); *E21B 43/116* (2013.01)

(58) Field of Classification Search
CPC .... G01N 33/24; G01N 33/241; G01N 33/383; E21B 49/02; E21B 43/116; E21B 49/006
See application file for complete search history.

(56) References Cited

U.S. PATENT DOCUMENTS 5,348,093 A * 9/1994 Wood .................... E21B 49/006
                                                 166/250.14
7,380,466 B2 * 6/2008 Deeg .................... G01N 33/383
                                                 73/803
2014/0007667 A1 * 1/2014 Haggerty ............. G01N 33/241
                                                 73/152.11
2014/0174192 A1   6/2014 Shine, Jr. et al.
2017/0205388 A1   7/2017 Thomas et al.

FOREIGN PATENT DOCUMENTS

CA        2777900 A1    5/2011

OTHER PUBLICATIONS

Supercement for Annular Seal and Long-Term Integrity in Deep, Hot Wells "DeepTrek" Kevin D. Edgley (Year: 2005).*
"Recommended Practices for Evaluation of Well Perforators," American Petroleum Institute (API), Sep. 2006, 66 pages, Distributed by Thomson Reuters.

(Continued)

*Primary Examiner* — Regis J Betsch
*Assistant Examiner* — Kaleria Knox
(74) *Attorney, Agent, or Firm* — John Wustenberg; Parker Justiss, P.C.

(57) ABSTRACT

Provided, in one aspect, is a method for performing a rock core flow performance test. The method, in this aspect, includes containing un-cured cement within an in-situ cement curing test fixture. The method additionally includes placing the in-situ cement curing test fixture with the un-cured cement within a pressure vessel of a rock core flow test system, and subjecting the in-situ cement curing test fixture with the un-cured cement within the pressure vessel to non-ambient temperature or pressure to form in-situ cured cement.

15 Claims, 9 Drawing Sheets

(56) References Cited

OTHER PUBLICATIONS

Ayre, D., et al., "API RP 19B Section 2 Perforation Tests Conducted at Multiple Facilities to Guide the Latest Section 2 Revision," SPE-187408-MS, SPE Annual Technical Conference and Exhibition, San Antonio, Texas, Oct. 9-11, 2017, Society of Petroleum Engineers, 22 pages.

Grove, B., et al., "Operators Optimize High-Pressure/High-Temperature and Ultrahigh-Pressure Perforation Strategies Using Laboratory Testing," OTC-29611-MS, Offshore Technology Conference, Houston, Texas, May 6-9, 2019, 22 pages.

* cited by examiner

METHOD AND APPARATUS FOR IN SITU CEMENT CURING

BACKGROUND

In order to predict a well's production, plan for well construction, and among other things, design a perforation tool and/or a downhole perforation procedure, one or more rock core samples that are considered to be representative of the subterranean formation may be tested in a laboratory setting. As those skilled in the art appreciate, such testing assists in determining certain parameters of the subterranean formation and/or interactions between the explosive charges, production tubing/casing, cement/annulus, and the subterranean formation. The test results may then be used in designing the wellbore configuration, wellbore perforation tool and/or the downhole perforation procedure.

BRIEF DESCRIPTION

Reference is now made to the following descriptions taken in conjunction with the accompanying drawings, in which.

DETAILED DESCRIPTION

Figure 1:
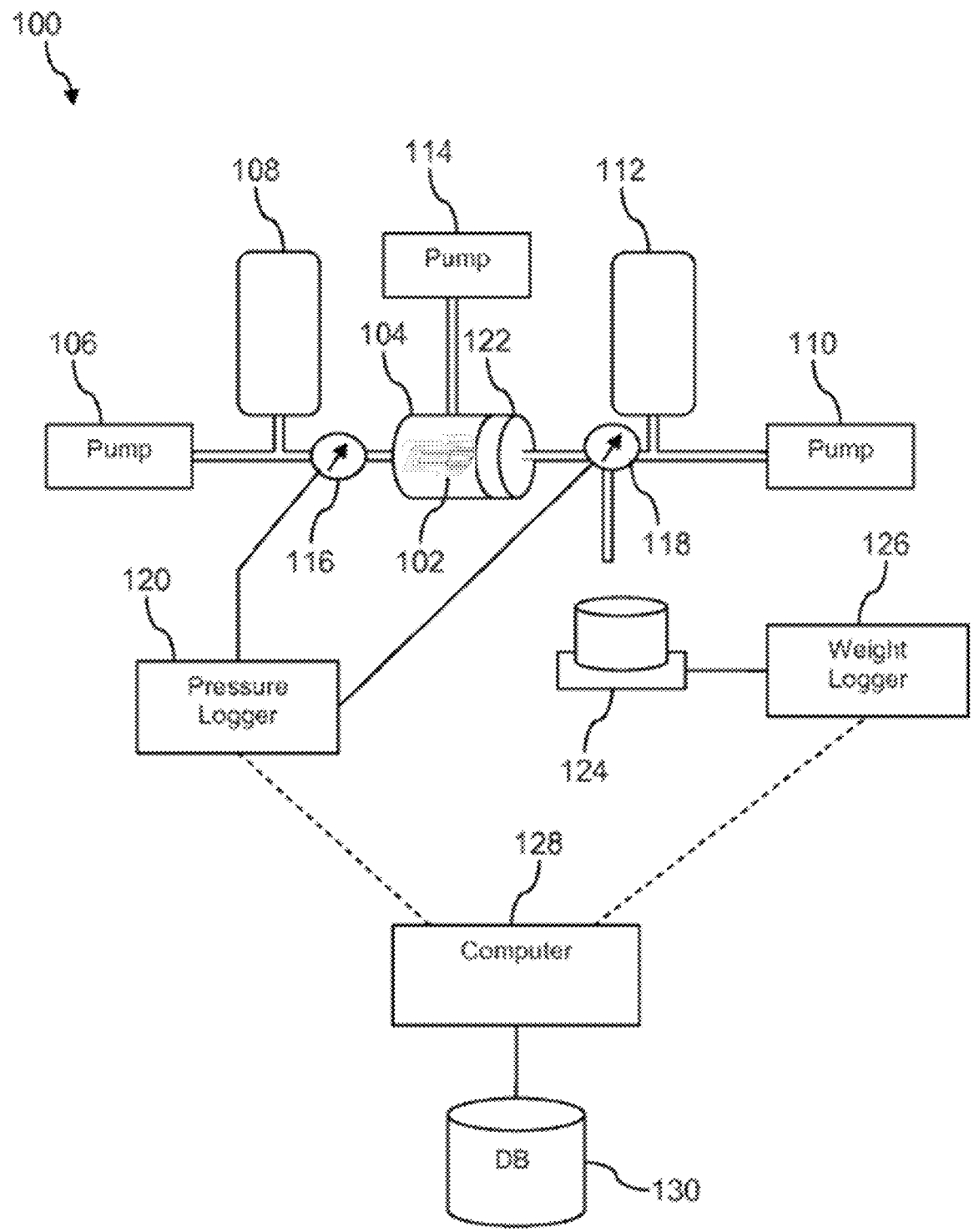
FIG. 1 illustrates an embodiment of a rock core flow test system manufactured and designed according to the disclosure.

It should be understood at the outset that although illustrative implementations of one or more embodiments are discussed below, the disclosed systems and methods may be implemented using any number of techniques, whether currently known or in existence. The disclosure should in no way be limited to the illustrative implementations, drawings, and techniques shown below, but may be modified within the scope of the appended claims along with their full scope of equivalents.

Unless otherwise specified, any use of any form of the terms "connect," "engage" "couple" "attach," or any other term describing an interaction between elements is not meant to limit the interaction to direct interaction between the elements and may also include indirect interaction between the elements described. The various characteristics mentioned above, as well as other features and characteristics described in more detail below, will be readily apparent to those skilled in the art with the aid of this disclosure upon reading the following detailed description of the embodiments, and by referring to the accompanying drawings.

Testing of rock core samples may be conducted to evaluate and to adjust well design, perforation gun design parameters and perforation procedure parameters. Testing may be conducted based on American Petroleum Institute (API) reference procedure 19B (API RP 19B), Recommended Practices for Evaluation of Well Perforators, First Edition, November 2000. Testing is typically performed on a rock core sample that is considered to be representative of the subterranean formation. For example, rock cuttings from a subterranean formation retrieved from the wellbore to be perforated may be captured and analyzed to determine characteristics of the rock of the subterranean formation. An outcrop rock may then be selected based on the similarity of its characteristics to the characteristics of the rock cuttings from the subterranean formation. The outcrop rock is trimmed to a form suitable for core testing, for example a circular cylinder form about 18 centimeters (e.g., a little over 7 inches) in diameter and about 70 centimeters (e.g., a little over 27 inches) in axial length, in one example. Other diameters and lengths, however, are within the scope of the disclosure. In some cases, a rock core sample may be extracted from the wellbore and used in rock core testing, but such core samples are expensive to obtain and are less and less frequently available.

The present disclosure contemplates performing at least some of the rock core sample testing using high temperature or high pressure conditions, as may be seen in some downhole environments. In accordance with the disclosure, at least the process of curing the cement may be conducted at non-ambient temperatures or pressures, or non-ambient temperatures and pressures. For example, in one embodiment, the curing of the cement may be conducted at temperatures or pressures similar to those that would likely be found proximate the reservoir of interest. In one embodiment, the un-cured cement is placed within an in-situ cement curing test fixture, which could then be placed within a pressure vessel of a rock core flow test system, to cure at the temperatures or pressures similar to those that would likely be found proximate the reservoir of interest. As the in-situ cement curing test fixture tends to be inverted (e.g., with the opening of the in-situ cement curing test fixture pointing at least partially downward) when placed within the pressure vessel, and thus the un-cured cement may be subject to escape, a sealant may be coupled over an opening thereof, thus retaining the un-cured cement within the in-situ cement curing test fixture until the in-situ cured cement is formed.

Turning now to FIG. 1, illustrated is one embodiment of a rock core flow test system 100 designed and manufactured according to the disclosure. In one or more embodiments, the rock core flow test system 100 includes a test assembly 102 positioned within a pressure vessel 104. In accordance with one embodiment, the test assembly 102 includes an in-situ cement curing test fixture, a perforation assembly positioned proximate the in-situ cement curing test fixture, a wellbore test structure surrounding the in-situ cement curing test fixture, and a rock core sample coupled with the in-situ cement curing test fixture.

The rock core flow test system 100 illustrated in FIG. 1 additionally includes a first pump 106, a first high pressure accumulator 108, a second pump 110, a second high pressure accumulator 112, and a third pump 114, among other elements. The rock core flow test system 100 may further include a first pressure sensor 116, a second pressure sensor 118, a high speed pressure logger 120, a fast opening high pressure flow control device 122, a scale 124, and a weight logger 126, again among other elements. In some contexts, the fast opening high pressure flow control device 122 may be referred to as a high speed high pressure flow control device. The pumps 106, 110, and 114 are capable of providing fluid at high pressure, for example fluid at pressures greater than about 5,000 pounds per square inch (PSI), 10,000 PSI, 15,000 PSI 20,000 PSI, 25,000 PSI, 30,000 PSI, 35,000 PSI, 40,000 PSI, 45,000 PSI, or 50,000 PSI. In one or more embodiments, the pumps 106, 110, and 114 may be capable of supplying fluid pressurized up to about 50,000 PSI. The pumps 106, 110, and 114 may be triplex type pumps, though, in other embodiments, a different type of pump may be employed. The pressure vessel 104, in accordance with the disclosure, may be capable of handling temperatures of at least about 37° C., 93° C., 148° C., 260° C., or more. In one embodiment, the increased temperatures are generated using one or more heat bands surrounding the pressure vessel 104. Nevertheless, the present disclosure should not be limited to any specific apparatus, or method, for generating the increased temperatures desired to conduct the cement curing process. The high pressures and high temperatures that the rock core flow test system 100 may achieve are consistent with the high pressures and high temperatures found proximate the reservoir of interest.

It is understood that the rock core flow test system 100 may contain components and equipment not explicitly described herein. For example, a flow distributor (not shown) may be coupled between the test assembly 102 and the first pump 106 and/or the first accumulator 108. High pressure piping may be used to couple components of the rock core flow test system 100 to each other. Check valves may be used to impose one-way flow directionality in some portions of the rock core flow test system 100. Pressure relief valves may be used to promote safety and/or to promote collecting fluid as an indication of fluid flow through the test assembly 102.

Figure 2A:
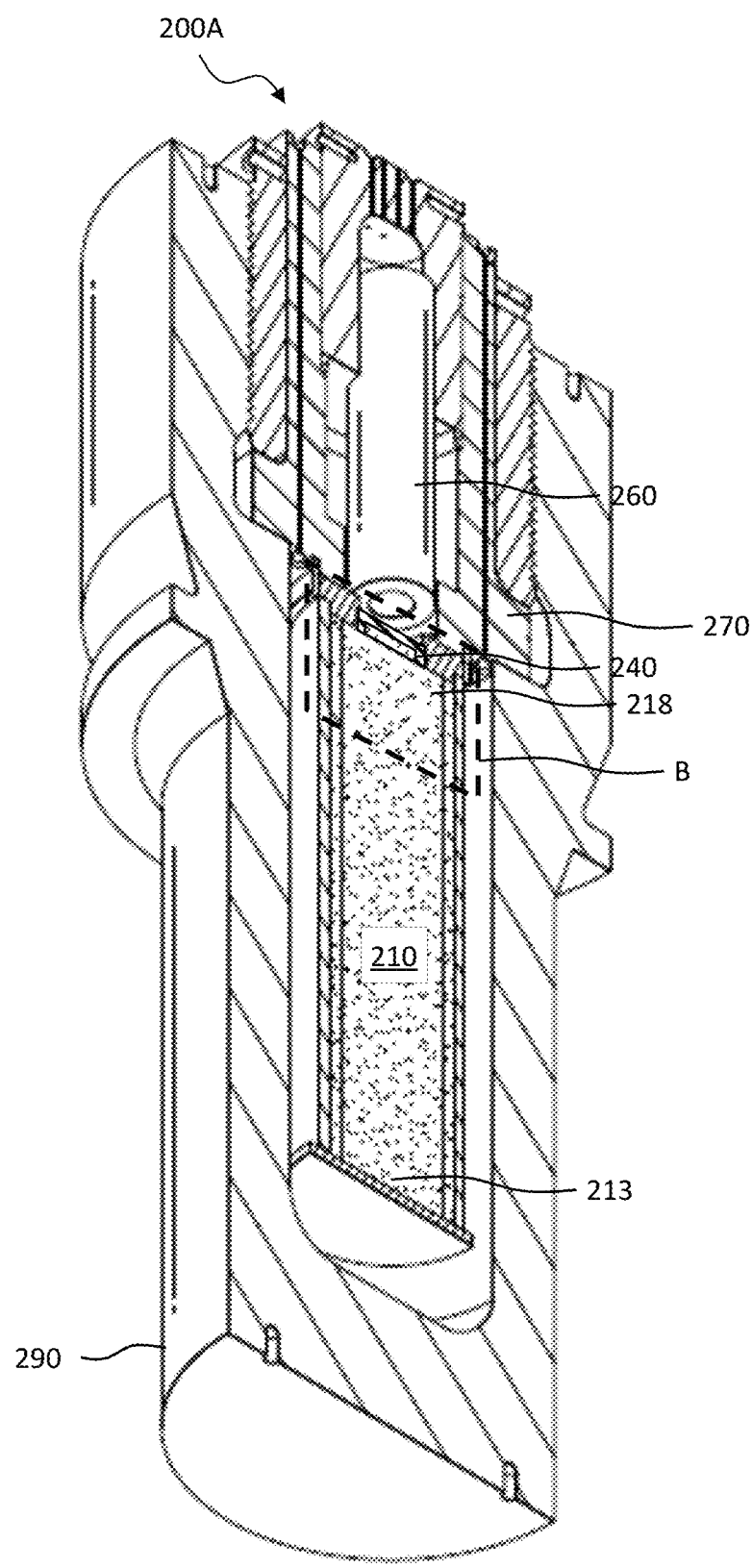
FIGS. 2A-2E illustrate various configurations of test assemblies manufactured and designed according to embodiments of the disclosure.

Turning to FIG. 2A, illustrated is test assembly 200A manufactured and designed according to embodiments of the disclosure. The test assembly 200A might be configured for use with the rock core flow test system 100 illustrated and described above with regard to FIG. 1, or another rock core flow test system according to the disclosure. In the embodiment illustrated in FIG. 2A, the test assembly 200A is positioned within a pressure vessel 290. Those skilled in the art understand the various different types of pressure vessels that may be used, including pressure vessels capable of handling and/or generating the aforementioned high pressures and temperatures.

The test assembly 200A, in the illustrated embodiment, includes a rock core sample 210. The rock core sample 210 shown in FIG. 2A includes a pore axial end 213 and a wellbore facing end 218. The rock core sample 210 may comprise a field core or analog core, among other cores, and remain within the scope of the present disclosure. The rock core sample 210, in accordance with the disclosure, will be of the type most likely to be found in the location of interest (e.g., where a customer might want to drill an oil/gas well), or alternatively an outcrop rock core sample representative of the type most likely to be found in the location of interest. Many materials for the rock core sample 210 are within the scope of the disclosure, and thus the disclosure should not be limited to any specific material.

Coupled to the rock core sample 210, in the embodiment of FIG. 2A, is an in-situ cement curing test fixture 240 manufactured and designed according to the disclosure. In the illustrated embodiment, the in-situ cement curing test fixture 240 is coupled to the wellbore facing end 218 of the rock core sample 210. While the embodiment illustrated in FIG. 2A shows that the in-situ cement curing test fixture 240 is directly coupled to the wellbore facing end 218 of the rock core sample 210, other embodiments may exist wherein the in-situ cement curing test fixture 240 is indirectly coupled to the wellbore facing end 218 of the rock core sample 210.

Positioned proximate the in-situ cement curing test fixture 240 is a perforation assembly 260. Those skilled in the art understand the various different types and styles of perforation assemblies 260 that might be used, and still remain within the scope of the present disclosure. In the illustrated embodiment, the in-situ cement curing test fixture 240 and the perforation assembly 260 are at least partially surrounded by a wellbore test structure 270.

Figure 2B:
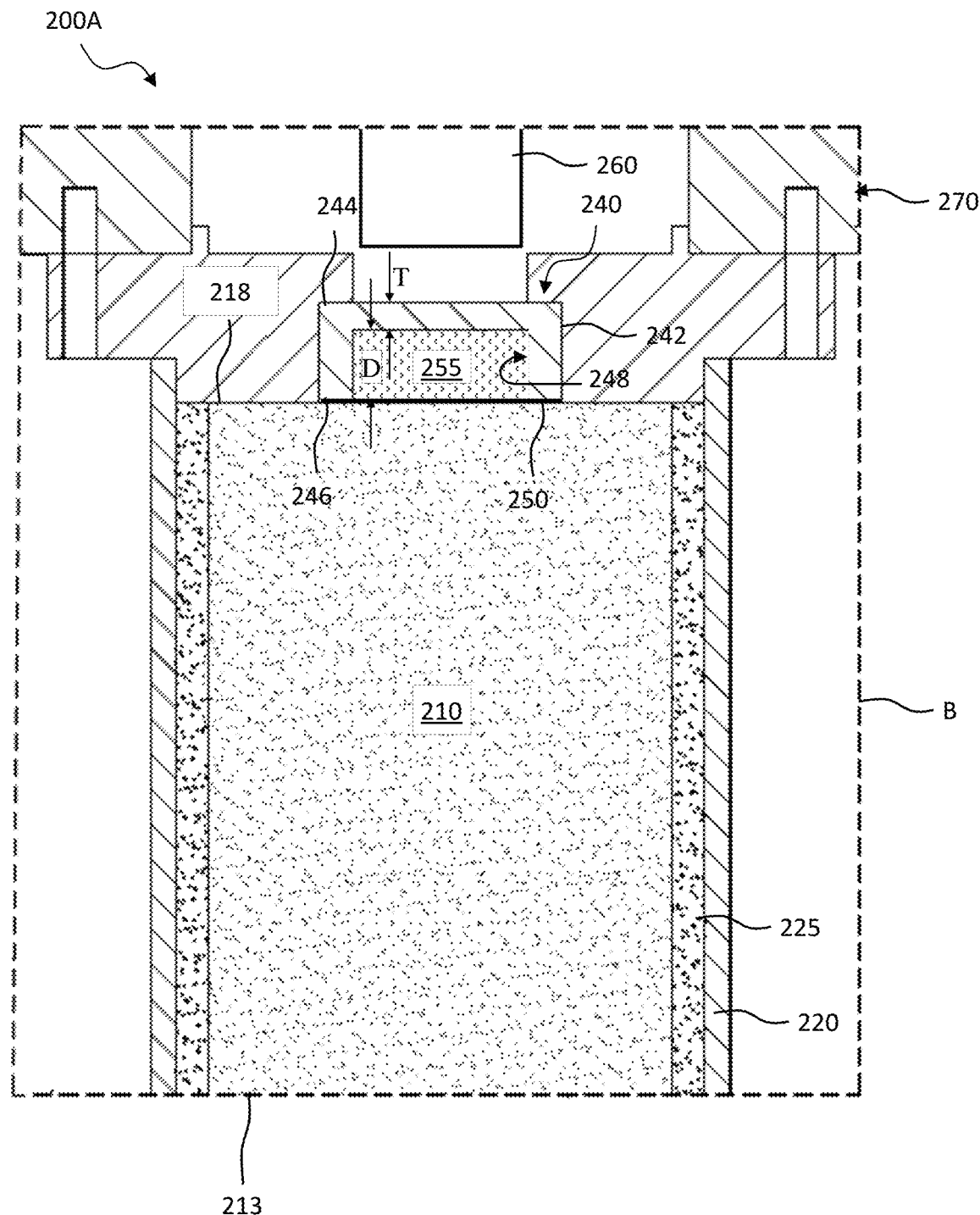

Turning now specifically to FIG. 2B, illustrated is a zoomed in view of the test assembly 200A, as taken from the dotted box B illustrated in FIG. 2A. The test assembly 200A includes the rock core sample 210 having the pore axial end 213 and a wellbore facing end 218. The test assembly 200A further includes a sleeve 220 (e.g., an impermeable sleeve, bladder, etc.) surrounding a longitudinal circumference of the rock core sample 210. The sleeve 220, in one embodiment, has an inner diameter a bit larger than the outer diameter of the rock core sample 210, such that an annular space exists between the inner diameter of the sleeve 220 and the outer diameter of the rock core sample 210. In one particular embodiment, the inner diameter of the sleeve 220 is about 1.25 cm larger than the outer diameter of the rock core sample 210. Accordingly, wherein the rock core sample 210 has a diameter of about 21.5 cm, the sleeve 220 might have an inner diameter of about 22.75 cm. Other embodiments exist, however, where no easily measurable space exists between the sleeve 220 and the rock core sample 210, or wherein the dimensions are different than those disclosed.

In the particular embodiment of FIG. 2B, a proppant 225 is placed within the annular space between the sleeve 220 and the rock core sample 210. The proppant 225 may be a filler material that is spaced substantially equidistance around the rock core sample 210. In at least one embodiment, rods are placed within the annular space such that the equidistance is created and the proppant 225 can then be placed therein. The proppant 225 may be uniform beads, such as ceramic, bauxite or any other suitable material.

The in-situ cement curing test fixture 240, in the illustrated embodiment, is positioned over the wellbore facing end 218 of the rock core sample 210. The in-situ cement curing test fixture 240, in accordance with the disclosure, includes a housing 242 having a first surface 244 and a second opposing surface 246. In accordance with one embodiment of the disclosure, an opening 248 exists within the housing 242, for example extending only partially from the second opposing surface 246 to the first surface 244. In accordance with the embodiment of FIG. 2B, the opening 248 defines a cup depth (D) and a cup base thickness (T). In accordance with one embodiment, the cup depth (D) simulates a desired downhole cement thickness and the cup base thickness (T) simulates a desired downhole wellbore casing thickness. Other in-situ cement curing test fixtures, different from that illustrated in FIG. 2B, are within the scope of the disclosure.

The in-situ cement curing test fixture 240, in the illustrated embodiment, additionally includes a sealant 250 coupled to the second opposing surface 246 and entirely covering the opening 248. The sealant 250, when employed, maintains un-cured cement within the opening 248 as the un-cured cement is being cured in a rock flow core test system, such as the rock flow core test system 100 illustrated in FIG. 1. The sealant 250 is particularly necessary when the in-situ cement curing test fixture 240 is inverted as shown in FIG. 2B (e.g., prior to the un-cured cement fully curing), or when the second opposing surface 246 is below the first surface 244 (e.g., again prior to the un-cured cement fully curing).

The sealant 250, in one embodiment, is a gasket. When used, an adhesive material may be located on a circumference of the second opposing surface 246 to couple the gasket to the housing 242. In another embodiment, the sealant 250 is a more rigid structure that is coupled to the second opposing surface 246 using one or more fasteners (not shown). Notwithstanding the foregoing, the sealant 250 would desirably have little to no resistance to the firing of the perforation tool 260, and thus not significantly affect the rock core flow performance test.

Positioned within the opening 248, and in the embodiment of FIG. 2B held within the opening 248 by the sealant 250, is un-cured cement 255. The phrase un-cured cement, as that term is used herein, refers to cement that is still at least partially in fluid form, and thus remains flowable. The un-cured cement 255, in accordance with one embodiment, will be of the type most likely used in the wellbore of interest.

The test assembly 200A additionally includes the perforation assembly 260 positioned proximate the first surface 244 of the in-situ cement curing test fixture 240. In the illustrated embodiment, the perforation assembly 260 is positioned directly above the first surface 244. In another embodiment, however, the perforation assembly 260 is positioned in direct contact with the first surface 244. The test assembly 200A additionally includes the wellbore test structure 270 at least partially surrounding the perforation assembly 260 and the in-situ cement curing test fixture 240. The wellbore test structure 270 illustrated in FIG. 2B includes multiple adjoined pieces. In other embodiments, however, the wellbore test structure 270 includes a single piece.

Figure 2C:
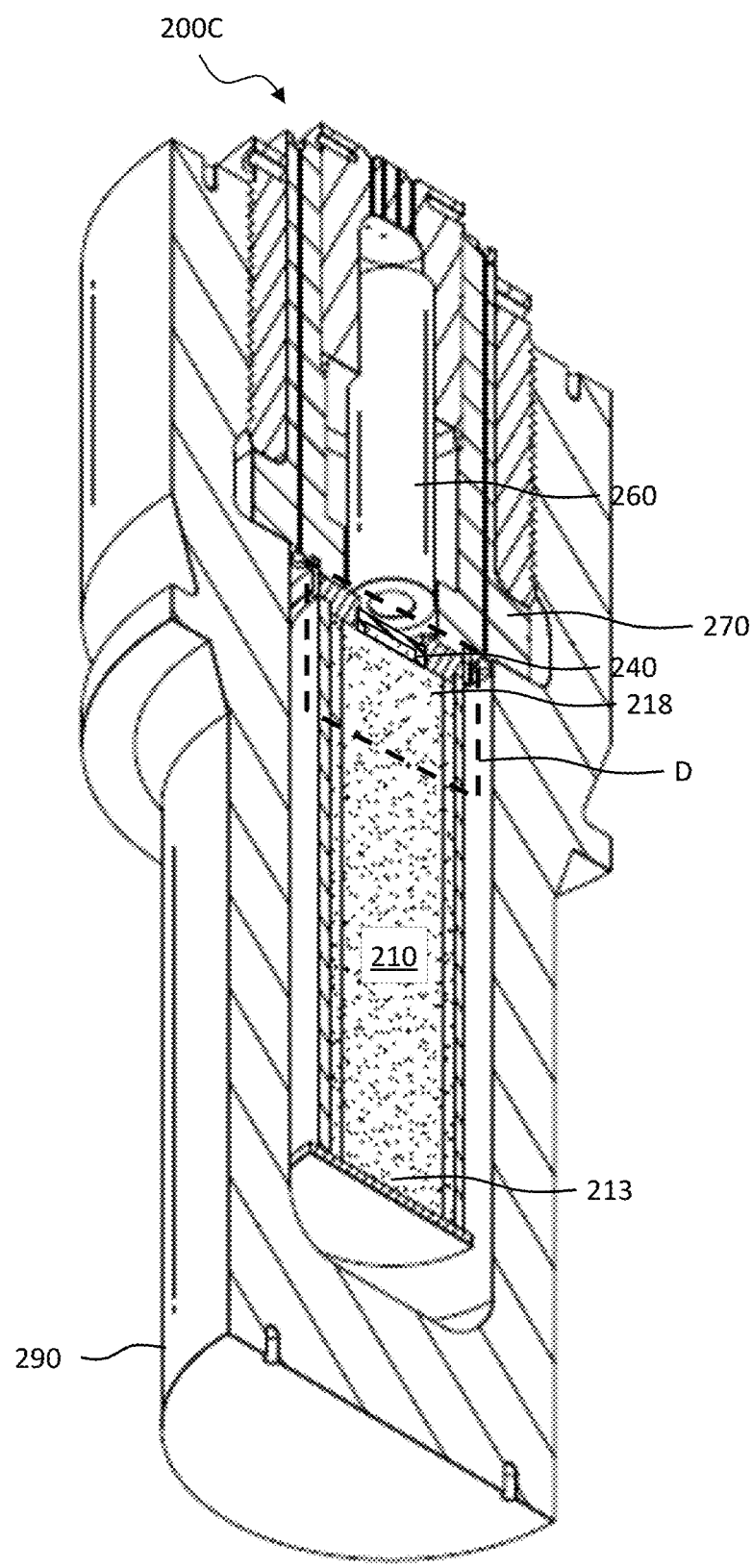
Figure 2D:
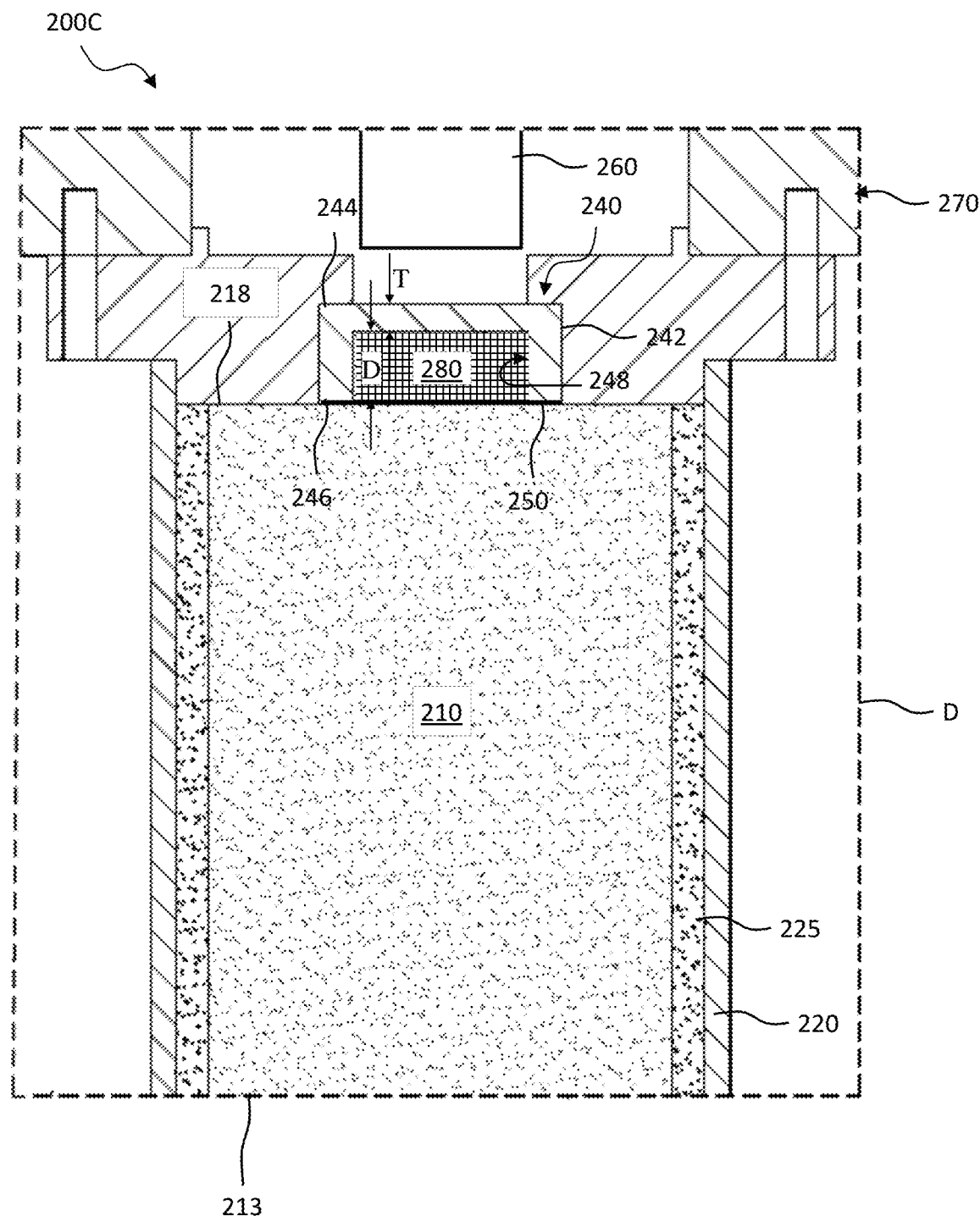

Turning now to FIGS. 2C and 2D, illustrated is a test assembly 200C, which represents the test assembly 200A of FIGS. 2A and 2B after subjecting the in-situ cement curing test fixture 240 with the un-cured cement 255 to non-ambient temperature and pressure via the pressure vessel 290. Such non-ambient temperatures and pressures may include one or both of temperatures above about 37° C., and more particularly temperatures above about 93° C., and/or pressures above about 500 PSI, and more particularly pressures above about 1000 PSI. Those skilled in the art, particularly given the details above with regard to FIG. 1, would understand the various different ways to increase the temperature and/or pressure. What results is in-situ cured cement 280, which in this embodiment is cured using pressures and temperatures that approximate the pressures and temperatures that might be found downhole in the zone of interest. The sealant 250, in the illustrated embodiment, is in direct contact with the in-situ cured cement 280. Nevertheless, other embodiments may exist wherein the sealant 250 is not in direct contact with the in-situ cured cement 280.

Figure 2E:
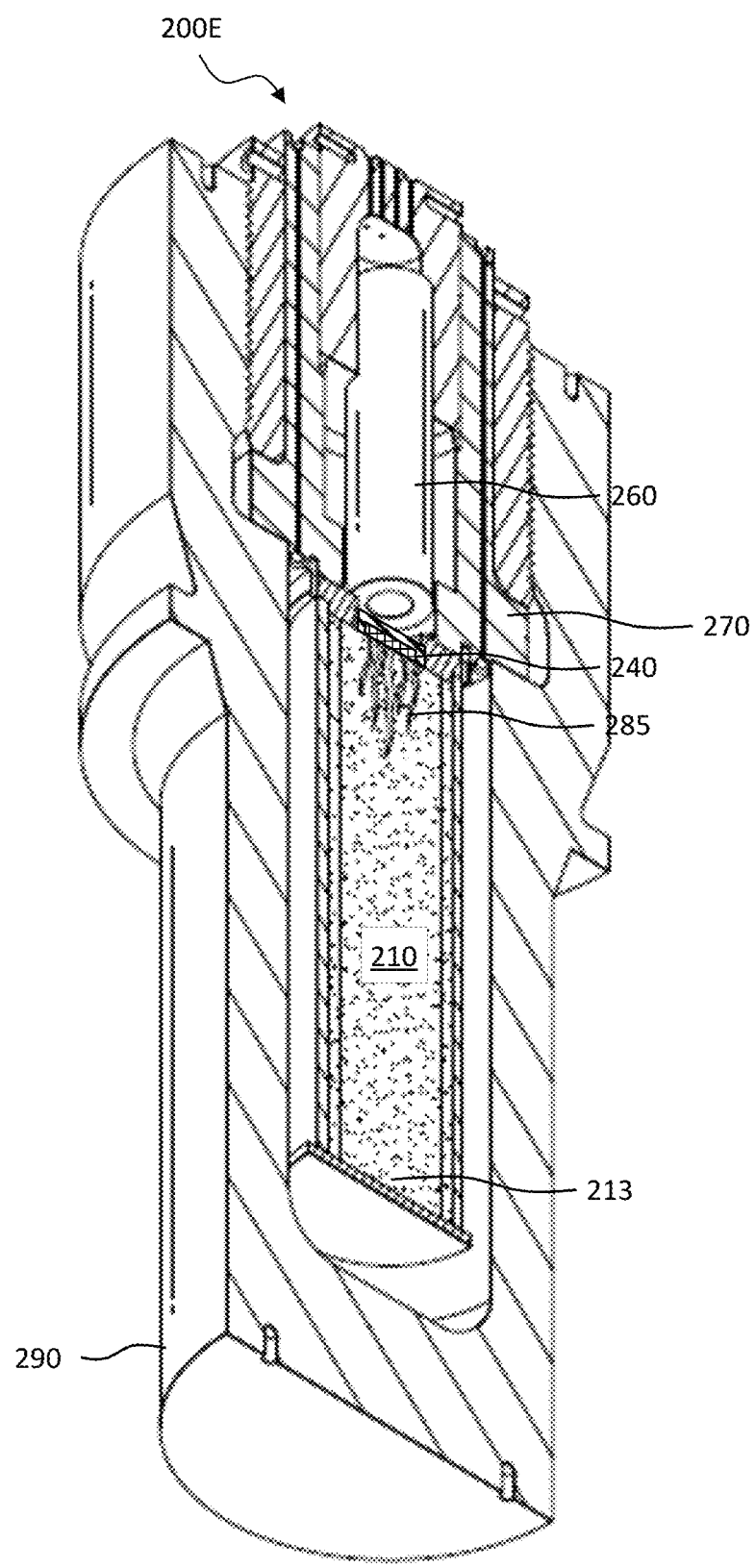

Turning now to FIG. 2E, illustrated is a test assembly 200E, which represents the test assembly 200C of FIGS. 2C and 2D after subjecting the in-situ cement curing test fixture 240 with the in-situ cured cement 280 to the perforation process. What results is the rock core sample 210 have one or more perforations 285 therein. The perforations, in this embodiment, should closely represent the perforations that may be found downhole, as for example the in-situ cured cement 280 best approximates the cement that might be found downhole.

Figure 3A:
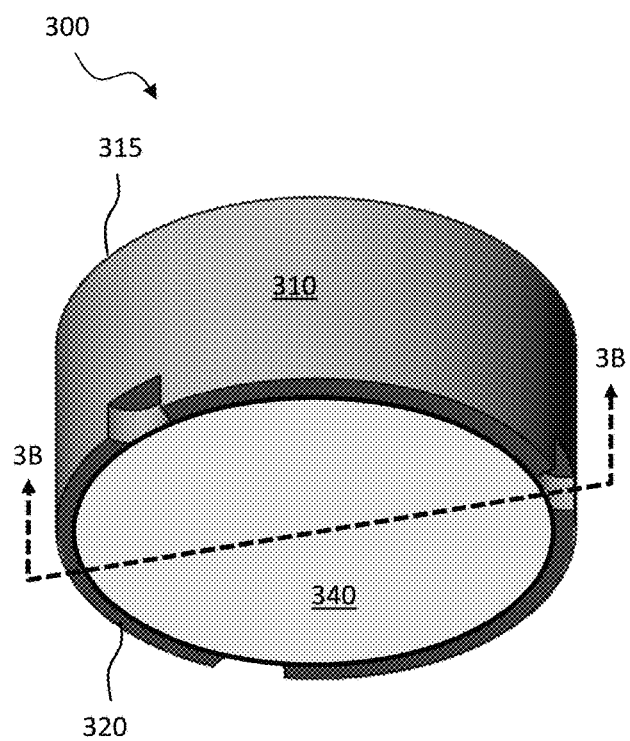
FIGS. 3A and 3B illustrate different views of an in-situ cement curing test fixture manufactured and designed according to the disclosure.
Figure 3B:
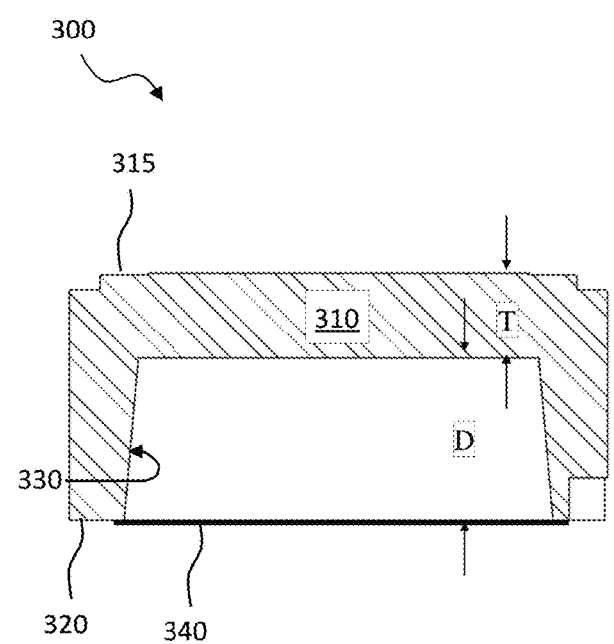

FIGS. 3A and 3B illustrate an in-situ cement curing test fixture 300 manufactured and designed according to another embodiment of the disclosure, wherein FIG. 3A illustrates a plan view of the in-situ cement curing test fixture 300 and FIG. 3B illustrates a cross-sectional of the in-situ cement curing test fixture 300 taken through the line 3B-3B. The in-situ cement curing test fixture 300 includes a housing 310 having a first surface 315 and a second opposing surface 320. The housing 310 may comprise many different materials and remain within the scope of the disclosure. In one embodiment, however, the housing 310 is steel, such as might be used for wellbore casing. In another embodiment, however, the housing 310 comprises a material having similar properties (e.g., metalurgical properties) as steel. The housing 310 may also comprise many different shapes and remain within the scope of the disclosure. In the illustrated embodiment, the housing 310 has a circular footprint. Other embodiments, however, may exist wherein the housing has a non-circular (e.g., a polygon in on embodiment) footprint.

The housing 310, in the embodiment of FIGS. 3A and 3B, includes an opening 330. The opening 330, in this embodiment, extends only partially from the second opposing surface 320 to the first surface 315. Accordingly, the opening 330 forms a cup, as might be used to contain un-cured cement. In accordance with one embodiment, the opening 330 defines a cup depth (D) that simulates a desired downhole cement thickness and a cup base thickness (T) that simulates a desired downhole wellbore casing thickness. Those skilled in the art understand the process for forming an appropriate opening 330, including the process for properly determining and creating the cup depth (D) and cup base thickness (T). In the illustrated embodiment of FIGS. 3A and 3B, one or more of the sidewall of the opening 330 slant outwardly from a base of the cup. Other embodiments may exist, however, where the one or more sidewalls do not slant at all, or alternatively slant inwardly toward the base of the cup.

The in-situ cement curing test fixture 300 illustrated in FIGS. 3A and 3B additionally includes a sealant 340. The sealant 340, in the illustrated embodiment, is coupled to the second opposing surface 320 and entirely covers the opening 330. Accordingly, the sealant 340 is configured to maintain un-cured cement within the opening 330 as the un-cured cement is being cured in a rock flow core test system, such as the rock flow core test system 100 illustrated in FIG. 1. The sealant 340, in the illustrated embodiment, is a gasket. For example, in this embodiment, the gasket is coupled to the housing 310 using one or more different types of adhesives located on a circumference of the second opposing surface 320. In an alternative embodiment, the sealant 340 is a more rigid structure, and may be coupled to the second opposing surface 320 using one or more fasteners.

Figure 4:
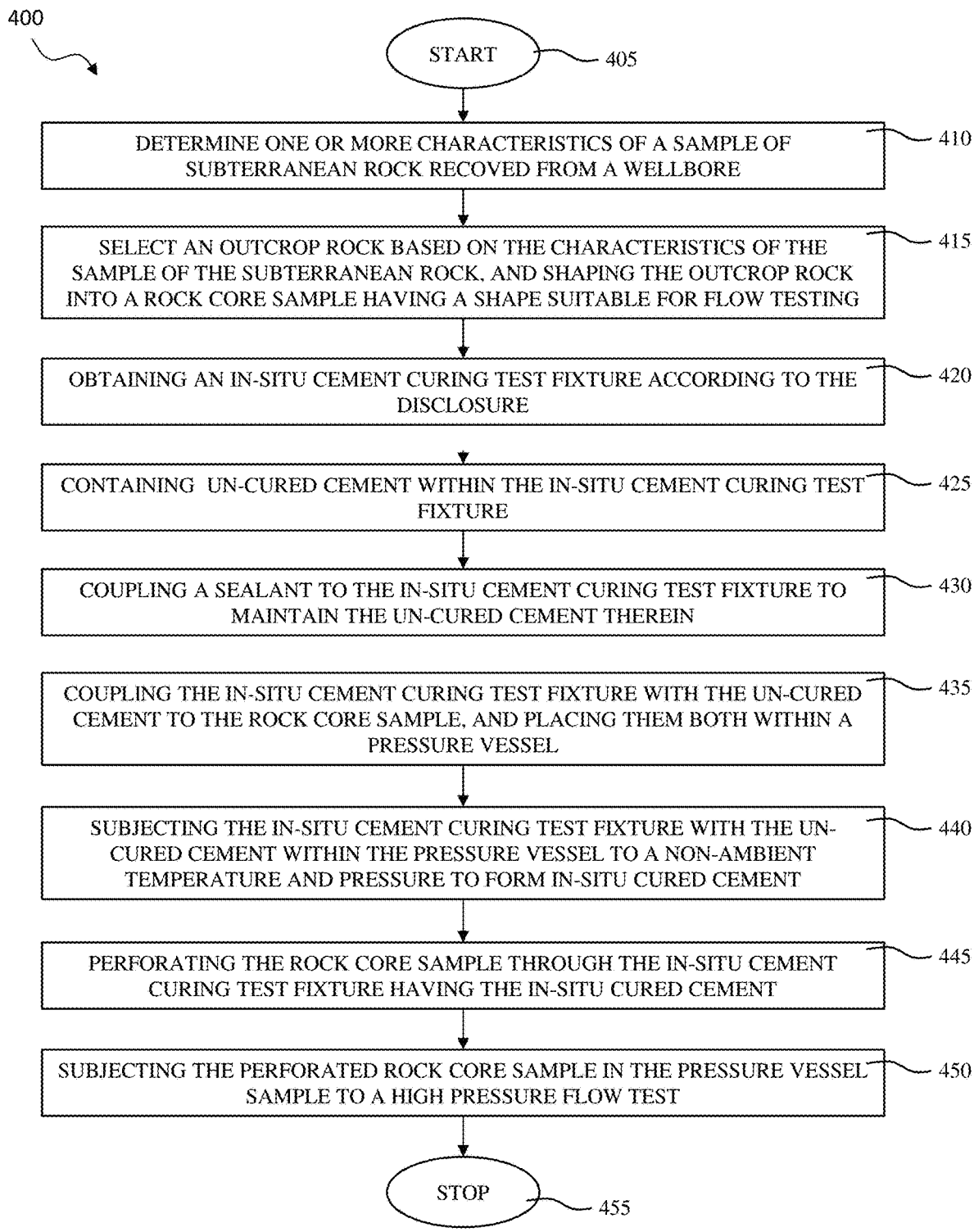
FIG. 4 illustrates a method of performing a rock core flow performance test in accordance with one embodiment of the disclosure.

Turning now to FIG. 4, one embodiment of a method of performing a rock core flow performance test 400 is described. In one or more embodiments, the method 400 may be employed to perform a transient pressure test. The method starts in a start step 405, and at step 410 one or more characteristics of a sample of subterranean rock are determined from the wellbore that is to be perforated. The characteristics may be the density of the rock, the permeability of the rock, the type of rock, and other relevant characteristics. At step 415, based on the characteristics of the sample of subterranean rock, an outcrop rock is selected that suitably models the subterranean rock, and the sample of outcrop rock is shaped into a rock core sample having a suitable shape for flow testing. For example, step 415 could include lathing the rock core sample (e.g., 210). It is understood that the rock core sample (e.g., 210) may be cut to any length and lathed to any diameter that is appropriate. The depth of the perforation expected to be created by the explosive charges of the perforation gun may be used to determine, at least in part, the length of the rock core sample (e.g., 210).

At step 420, an in-situ cement curing test fixture (e.g., 240) according to the disclosure is obtained. The in-situ cement curing test fixture (e.g., 240) is described in more detail above. In a step 425, un-cured cement (e.g., 255) is poured with an opening of the in-situ cement curing test fixture (e.g., 240), and in a step 430 a sealant (e.g. 250) is coupled over the opening to keep the un-cured cement (e.g., 255) therein. Step 430 is an optional step, which in certain embodiments may only be undertaken if the in-situ cement curing test fixture (e.g., 240) is inverted prior to the un-cured cement curing. At step 435, the in-situ cement curing test fixture (e.g., 240) and a perforation assembly (e.g., 260) are coupled to the rock core sample (e.g., 210), and then the in-situ cement curing test fixture (e.g., 240), the perforation assembly (e.g., 260), and the rock core sample (e.g., 210) are placed with a pressure vessel (e.g., 290). In certain embodiments, the in-situ cement curing test fixture (e.g., 240) having the sealant (e.g., 250) is rotated such that the second opposing surface is below the first surface after coupling the sealant (e.g., 250) and prior to subjecting the in-situ curing test assembly (e.g., 240) to non-ambient temperature and pressure. This rotation may occur before, or after, placing the in-situ cement curing test fixture (e.g., 240) with the un-cured cement within the pressure vessel (e.g., 290).

In accordance with the disclosure, in step 440, the in-situ cement curing test fixture (e.g., 240) having the un-cured cement (e.g., 255) therein is subjected to a non-ambient temperature and pressure to form in-situ cured cement (e.g., 280). Such non-ambient temperatures and pressures may include one or both of temperatures above about 37° C., and more particularly temperatures above about 93° C., and/or pressures above about 500 PSI, and more particularly pressures above about 1000 PSI. At step 445, with the in-situ cured cement (e.g., 280) in place, the perforation assembly (e.g., 260) is activated to perforate the rock core sample, for example through the in-situ cement curing test fixture (e.g., 240) having the in-situ cured cement (e.g., 280) therein. At step 450, a high pressure flow test is performed on the perforated rock core sample (e.g., 210).

With brief reference back to FIG. 1, the processing of step 450 may involve the computer 128 downloading data from the pressure logger 120 and/or from the weight logger 126 and analyzing this data. Alternatively, the data may be streamed from the pressure logger 120 and/or the weight logger 126 as the data is captured by these loggers 120, 126. The computer 128 may further determine flow rates through the rock core sample at different times during the high pressure flow test of the perforated rock core sample. The flow rates may be determined based on the weight samples downloaded from the weight logger 126 and based on compensating for compression effects of the fluid flowed in the rock core sample 102. For example, a table that defines fluid compression ratios at different pressures may be referenced by a compensation application executed by the computer 128. A fluid compression ratio may be proportional to the ratio of the volume of a unit mass of the subject fluid at a standard pressure such as atmospheric pressure to the volume of the unit mass of the subject fluid at an elevated pressure, such as at a pressure of 30,000 PSI. Alternatively, the fluid compression ratio may be proportional to the ratio of the volume of a unit mass of the subject fluid at an elevated pressure to the volume of the unit mass of the subject fluid at standard pressure.

The table may define the compression ratio of the subject fluid at each of 5000 PSI, 10000 PSI, 15000 PSI, 20000 PSI, 250000 PSI, 30000 PSI, 35000 PSI, 40000 PSI, 45000 PSI, 50000 PSI, 55000 PSI, and 60000 PSI. In another embodiment, the table may define more or fewer entries. The table may define different pressure indices, for example non-evenly spaced pressure indices. Rather than a table having entries of evenly spaced pressure indices, the table may have entries of evenly spaced compression ratios and corresponding pressure indices associated with each compression ratio. For values of pressure between the table entries, the compression ratio to apply may be linearly interpolated between the two closest pressure indices in the table or interpolated by another method. The method would ultimately end in a stop step 455.

Figure 5:
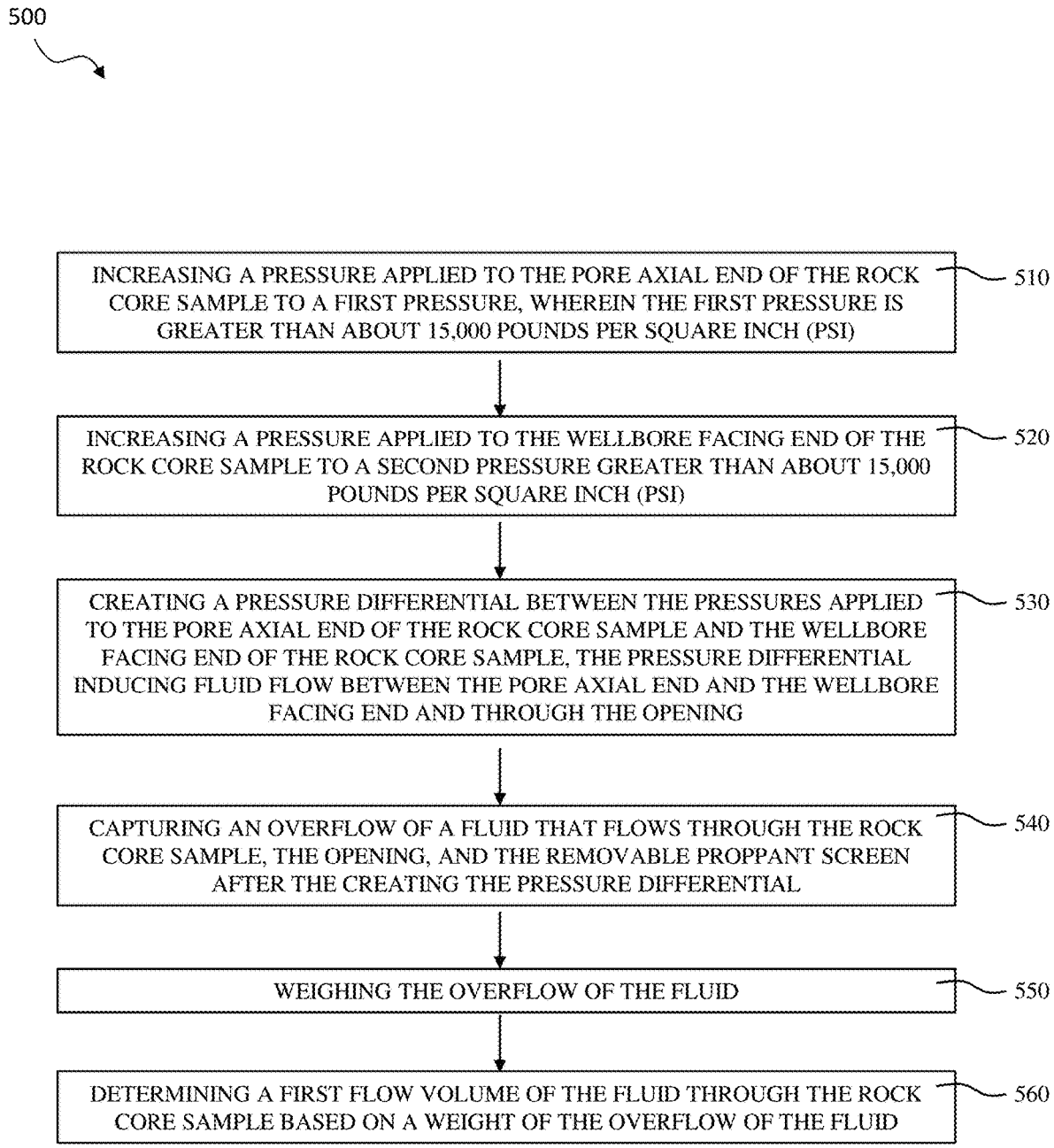
FIG. 5 illustrates a process flow, which expands step 450 of FIG. 4 into sub-steps.

Turning now briefly to FIG. 5, illustrated is a process flow 500, which expands step 450 of FIG. 4 into sub-steps. The process flow 500 begins in a step 510, wherein a pressure applied to the pore axial end (e.g., 213) of the rock core sample (e.g., 210) is increased to a first pressure, wherein the first pressure is greater than about 15,000 pounds per square inch (PSI). In a step 520, a pressure applied to the wellbore facing end (e.g., 218) of the rock core sample (e.g., 210) is increased to a second pressure greater than about 15,000 pounds per square inch (PSI). Steps 510 and 520 may be conducted in reverse order. In another example embodiment, steps 510 and 520 are conducted at the same time, and further their pressures are maintained substantially equal as the increase to the first pressure.

Thereafter, in a step 530, a pressure differential between the pressures applied to the pore axial end (e.g., 213) of the rock core sample (e.g., 210) and the wellbore facing end (e.g., 218) of the rock core sample (e.g., 210) may be created. This pressure differential induces fluid flow between the pore axial end (e.g., 213) and the wellbore facing end (e.g., 218). For example, the pressure differential may be formed by reducing the pressure applied to one of the pore axial end (e.g., 213) or wellbore facing end (e.g., 218) of the rock core sample (e.g., 210) while maintaining the pressure applied to the other of the wellbore facing end (e.g., 218) or pore axial end (e.g., 213) of the rock core sample (e.g., 210). In one example embodiment, a fast opening flow control device (e.g., 122) is fluidly coupled to the wellbore facing end (e.g., 218) of the rock core sample (e.g., 210), and the fast opening flow control device (e.g., 122) is actuated to create the threshold pressure differential.

In a step 540, an overflow of a fluid that flows through the rock core sample (e.g., 210) is captured after creating the pressure differential, and in a step 550 the overflow of the fluid is weighed. With this information in hand, a first flow volume of the fluid through the rock core sample (e.g., 210) is determined based on a weight of the overflow of the fluid in a step 560.

Aspects disclosed herein include:

A. A method for performing a rock core flow performance test, the method including containing un-cured cement within an in-situ cement curing test fixture, placing the in-situ cement curing test fixture containing the un-cured cement within a pressure vessel of a rock core flow test system, subjecting the in-situ cement curing test fixture with the un-cured cement within the pressure vessel to non-ambient temperature or pressure to form in-situ cured cement.

B. An in-situ cement curing test fixture, the in-situ cement curing test fixture including a housing having a first surface and a second opposing surface, an opening extending only partially from the second opposing surface to the first surface, the opening defining a cup depth (D) that simulates a desired downhole cement thickness and a cup base thickness (T) that simulates a desired downhole wellbore casing thickness, and a sealant coupled to the second opposing surface and entirely covering the opening for maintaining cement within the opening as the cement is being cured in a rock flow core test system.

C. A rock core flow test system, the rock core flow test system including a pressure vessel, and a test assembly positioned within the pressure vessel, the test assembly including: 1) an in-situ cement curing test fixture, comprising: a) a housing having a first surface and a second opposing surface, b) an opening extending only partially from the second opposing surface to the first surface, the opening defining a cup depth (D) that simulates a desired downhole cement thickness and a cup base thickness (T) that simulates a desired downhole wellbore casing thickness, c) in-situ cured cement positioned within the opening, and d) a sealant coupled to the second opposing surface and entirely covering the opening; 2) a perforation assembly positioned proximate the first surface, 3) a wellbore test structure surrounding the perforation assembly and the in-situ cement curing test fixture, and 4) a rock core sample having a pore axial end and a wellbore facing end, and further wherein the wellbore facing end is coupled with the second opposing surface.

Aspects A, B, and C may have one or more of the following additional elements in combination: Element 1: further including coupling a rock core sample to the in-situ cement curing test fixture containing the un-cured cement prior to subjecting the in-situ cement curing test fixture with the un-cured cement within the pressure vessel to non-ambient temperature or pressure. Element 2: further including perforating the rock core sample through the in-situ cement curing test fixture having the in-situ cured cement. Element 3: further including subjecting the perforated rock core sample to a flow test. Element 4: wherein subjecting the perforated rock core sample to a flow test includes: increasing a pressure applied to a pore axial end of the rock core sample to a first pressure, wherein the first pressure is greater than 15,000 pounds per square inch (PSI); increasing a pressure applied to a wellbore facing end of the rock core sample to a second pressure greater than 15,000 pounds per square inch (PSI); creating a pressure differential between the pressures applied to the pore axial end of the rock core sample and the wellbore facing end of the rock core sample, the pressure differential inducing fluid flow between the pore axial end and the wellbore facing end and through the in-situ cement curing test fixture; capturing an overflow of a fluid that flows through the rock core sample and the in-situ cement curing test fixture after the creating the pressure differential; weighing the overflow of the fluid; and determining a flow volume of the fluid through the rock core sample based on a weight of the overflow of the fluid. Element 5: further including coupling a sealant to the in-situ cement curing test fixture to maintain the un-cured cement therein prior to placing the in-situ cement curing test fixture with the un-cured cement within the pressure vessel. Element 6: further including rotating the in-situ cement curing test fixture such that the sealant is below the un-cured cement prior to subjecting the in-situ curing test assembly to the non-ambient temperature or pressure. Element 7: wherein rotating includes rotating after placing the in-situ cement curing test fixture with the un-cured cement within the pressure vessel and before subjecting the in-situ cement curing test fixture with the un-cured cement within the pressure vessel to non-ambient temperature and pressure. Element 8: wherein coupling a sealant to the in-situ cement curing test fixture includes coupling a gasket to the in-situ cement curing test fixture. Element 9: further including applying an adhesive material to a circumference of the in-situ cement curing test fixture and then coupling the gasket to the in-situ cement curing test fixture using the adhesive material. Element 10: wherein the sealant is a gasket. Element 11: further including an adhesive material located on a circumference of the second opposing surface to couple the gasket to the housing. Element 12: wherein further including one or more fasteners coupling the sealant to the second opposing surface. Element 13: wherein the sealant is in direct contact with the in-situ cured cement.

Those skilled in the art to which this application relates will appreciate that other and further additions, deletions, substitutions and modifications may be made to the described embodiments.

What is claimed is:

1. A method for performing a rock core flow performance test, comprising:
   containing un-cured cement within an in-situ cement curing test fixture;
   placing the in-situ cement curing test fixture containing the un-cured cement within a pressure vessel of a rock core flow test system; and
   subjecting the in-situ cement curing test fixture with the un-cured cement within the pressure vessel, the in-situ cement curing test fixture coupled to a rock core sample, to non-ambient temperature or pressure to form in-situ cured cement.

2. The method as recited in claim 1, further including perforating the rock core sample through the in-situ cement curing test fixture having the in-situ cured cement.

3. The method as recited in claim 2, further including subjecting the perforated rock core sample to a flow test.

4. The method as recited in claim 3, wherein subjecting the perforated rock core sample to a flow test includes:
   increasing a pressure applied to a pore axial end of the rock core sample to a first pressure, wherein the first pressure is greater than 15,000 pounds per square inch (PSI);
   increasing a pressure applied to a wellbore facing end of the rock core sample to a second pressure greater than 15,000 pounds per square inch (PSI);
   creating a pressure differential between the pressures applied to the pore axial end of the rock core sample and the wellbore facing end of the rock core sample, the pressure differential inducing fluid flow between the pore axial end and the wellbore facing end and through the in-situ cement curing test fixture;
   capturing an overflow of a fluid that flows through the rock core sample and the in-situ cement curing test fixture after the creating the pressure differential;
   weighing the overflow of the fluid; and
   determining a flow volume of the fluid through the rock core sample based on a weight of the overflow of the fluid.

5. The method as recited in claim 1, further including coupling a sealant to the in-situ cement curing test fixture to maintain the un-cured cement therein prior to placing the in-situ cement curing test fixture with the un-cured cement within the pressure vessel.

6. The method as recited in claim 5, further including rotating the in-situ cement curing test fixture such that the sealant is below the un-cured cement prior to subjecting the in-situ curing test assembly to the non-ambient temperature or pressure.

7. The method as recited in claim 6, wherein rotating includes rotating after placing the in-situ cement curing test fixture with the un-cured cement within the pressure vessel and before subjecting the in-situ cement curing test fixture with the un-cured cement within the pressure vessel to non-ambient temperature and pressure.

8. The method as recited in claim 5, wherein coupling a sealant to the in-situ cement curing test fixture includes coupling a gasket to the in-situ cement curing test fixture.

9. The method as recited in claim 8, further including applying an adhesive material to a circumference of the in-situ cement curing test fixture and then coupling the gasket to the in-situ cement curing test fixture using the adhesive material.

10. A rock core flow test system, comprising:
a pressure vessel; and
a test assembly positioned within the pressure vessel, the test assembly including:
an in-situ cement curing test fixture, comprising:
a housing having a first surface and a second opposing surface;
an opening extending only partially from the second opposing surface to the first surface, the opening defining a cup depth (D) that simulates a desired downhole cement thickness and a cup base thickness (T) that simulates a desired downhole wellbore casing thickness;
in-situ cured cement positioned within the opening; and
a sealant coupled to the second opposing surface and entirely covering the opening;
a perforation assembly positioned proximate the first surface;
a wellbore test structure surrounding the perforation assembly and the in-situ cement curing test fixture; and
a rock core sample having a pore axial end and a wellbore facing end, and further wherein the wellbore facing end is coupled with the second opposing surface.

11. The rock core flow test system as recited in claim 10, further including a first high pressure accumulator coupled to the pressure vessel and in fluid communication with the pore axial end of the rock core sample, and a second high pressure accumulator coupled to the pressure vessel and in fluid communication with the wellbore facing end of the rock core sample.

12. The rock core flow test system as recited in claim 10, wherein the sealant is a gasket.

13. The rock core flow test system as recited in claim 12, further including an adhesive material located on a circumference of the second opposing surface to couple the gasket to the housing.

14. The rock core flow test system as recited in claim 10, further including one or more fasteners coupling the sealant to the second opposing surface.

15. The rock core flow test system as recited in claim 10, wherein the sealant is in direct contact with the in-situ cured cement.

* * * * *